United States Patent [19]

Brunvoll

[11] Patent Number: 4,457,128
[45] Date of Patent: Jul. 3, 1984

[54] NEEDLE DEVICE FOR SPLICING

[76] Inventor: Lars Brunvoll, ovre Fredlundveg 37, N-5032 Minde, Norway

[21] Appl. No.: 432,924
[22] PCT Filed: Feb. 4, 1982
[86] PCT No.: PCT/NO82/00003
 § 371 Date: Sep. 30, 1982
 § 102(e) Date: Sep. 30, 1982
[87] PCT Pub. No.: WO82/02729
 PCT Pub. Date: Aug. 19, 1982

[30] Foreign Application Priority Data

Feb. 6, 1981 [NO] Norway .................................. 810405

[51] Int. Cl.³ .......................... D07B 7/18; B65H 69/06
[52] U.S. Cl. ........................................................ 57/23
[58] Field of Search ............................. 57/202, 22, 23

[56]  References Cited

U.S. PATENT DOCUMENTS

| 431,416 | 7/1890 | Todd | 57/23 |
|---|---|---|---|
| 1,542,656 | 6/1925 | Balod | 57/23 |
| 1,678,361 | 7/1928 | Shearon | 128/339 |
| 2,112,176 | 3/1938 | Olsson | 57/23 |
| 3,592,196 | 7/1971 | Daikhovsky | 128/339 |
| 4,158,281 | 6/1979 | Morang | 57/23 |

FOREIGN PATENT DOCUMENTS

| 2757524 | 6/1979 | Fed. Rep. of Germany | 57/23 |
|---|---|---|---|
| 170776 | 3/1960 | Sweden . | |

Primary Examiner—John Petrakes
Attorney, Agent, or Firm—Birch, Stewart, Kolasch & Birch

[57] ABSTRACT

A needle device for finishing and splicing lines or cordage consists essentially of a unitary member of substantially cylindrical configuration having a tapered front end, a tubular middle portion for receiving a strand end and a substantially tubular rear portion. The rear portion includes an elongated lateral opening and an integral hook internal thereof opposite the opening. The tip of the hook is spaced a distance from the middle portion sufficient to permit insertion of the strand into the middle portion. The strand may also be inserted laterally into the rear portion into engagement with the hook.

8 Claims, 6 Drawing Figures

NEEDLE DEVICE FOR SPLICING

The present invention relates to a needle device for the finishing of lines or cordage, especially for the splicing of rounded-plaited lines or braided cordage, comprising an end portion tapered at the front and a pipe portion directed rearwardly from the end portion, the opposite end of which is open for the endways reception of the end of the line or the strand end of the cordage.

The present invention is especially appropriate for use in splicing so-called round-plaited line, that is to say a line which on axial compression or clenching together forms an axially extending central hollow space together with relatively large lateral openings between the braided filaments to said central hollow space. In this way there can be formed a spliced noose on the end of the line by for example threading the line initially S-shaped right through a line portion and by conclusion threading the outer end of the line axially inwards into said central hollow space, the outer end of the line is finished internally screened in said line portion. Correspondingly spliced loops or other splice connections can also be fashioned for example in conventional braided cordage.

From U.S. Pat. No. 4,158,281 a needle is known for the afore-mentioned purpose. A needle is shown which, outside the rear pipe end, is provided with two opposite hook portions which are adapted to be tightened against an intermediate line end from each of its mutually opposite sides. After the hook portions are fixed to the line end, the hook portions and the line end are introduced a distance within the pipe end by turning the needle about its own axis relative to the hook portions and the line end fastened thereto. On dismantling the line end from the needle the hook portions and the associated line end must correspondingly first be turned relative to the needle and thereafter the hook portions opened relative to each other for withdrawal of the line end.

The known needle has a relatively complicated construction and is relatively complicated to use, the fastening in position of the line end in the needle and the releasing of the line end from the needle being relatively time-consuming work. In addition several problems can arise in the fastening and releasing of the line end under normal, relatively cool or cold working conditions at sea or under difficult working conditions, the fastening or releasing demanding great dexterity.

The present invention provides a needle with a far simpler construction and with a far simpler mode of operation, so that the splicing operations can be carried out in an easier and more rapid fashion than hitherto possible. An objective is to be able to produce the needle so cheaply that it can for example be included as standard equipment for a roll of rigging or other suitable rope portion length which is purchased by a user.

The device according to the invention is characterized in that the pipe portion has at its rear end an elongate laterally directed opening for the reception of the end of the line or the strand end of the cordage in the pipe portion of the needle, and in that from the bottom side of the pipe portion, adjacent the laterally directed opening, there project one or more hook portions obliquely upwards towards the laterally directed opening and obliquely forwards relative to the rear end of the pipe portion, the distance from the inner boundary edge of the opening to the outer end of the hook portion being somewhat larger than the diameter of the line or strand.

By means of the simple design of the needle according to the invention, moving parts are avoided, and there is the possibility for mounting the line end or the strand end in the open end of the needle and correspondingly dismantling the line end from the needle, when this is necessary, by means of a simple hand grip. Using a device according to the invention one is not dependent upon having to use the fingers to readjust movable locking means or other movable portions of the needle, but can, while the needle is received in one hand, stick the line end or the strand end, while the latter is received in the other hand, into position in the pipe end of the needle, and by a pivotal movement press this into position in a secure locking engagement with the hook portion of the needle. By a corresponding reverse pivoting of the line or the strand portion and subsequently withdrawing the latter in a direction obliquely outwards from the needle the line end or the strand end can similarly be easily released from the needle.

The simple manual handling of the needle is of great significance in splicing work and like finishing of the line or cordage outdoors in a cold climate, and is also of great importance in the splicing or other finishing of lines of small diameter where the needle is designed with a correspondingly small diameter. With needles of small diameter movable locking means would be rather difficult to handle.

As a consequence of the simple design of the needle, which is without moving parts, there is also the possibility of being able to design the needle in a relatively robust and operatively reliable manner even for needles which are used for rather thin lines.

According to the invention it can be ensured in a simple manner that the line is held in position in engagement with the hook portion of the needle, by designing, according to a preferred embodiment, the laterally directed opening over about ⅓ of the periphery of the pipe portion. Edge portions of the opening can thereby form holding means for securing the line in the pipe portion in front as well as behind the hook portion and close by the hook portion. In order to introduce the line into the pipe portion and to release the line from the needle respectively, the line must consequently be deformed to a certain degree in the lateral direction. In practice such a deformation proves sufficient to ensure that the line is in position in the needle during use, without thereby complicating the insertion and the withdrawal of the line to a significant degree.

Further features of the invention will be evident from the following description having regard to the accompanying drawings, in which.

Figure 1:
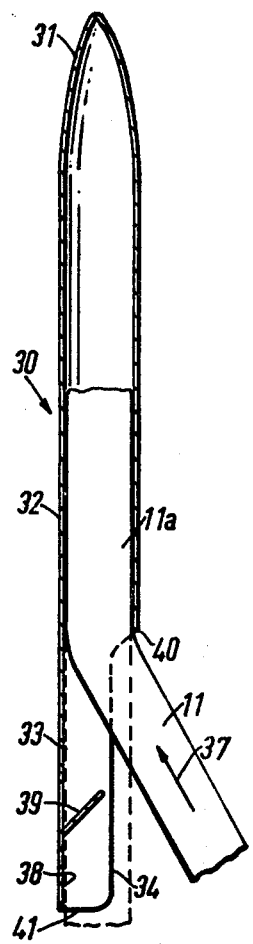
FIG. 1 shows a first embodiment of the needle produced from thin-walled metal, illustrated in a longitudinal section.
Figure 2:
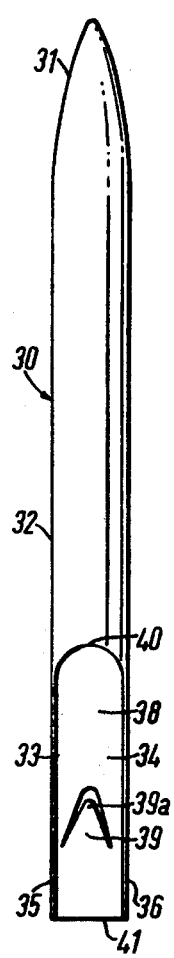
FIG. 2 shows the needle of FIG. 1 seen from the right side of FIG. 1.
Figure 3:
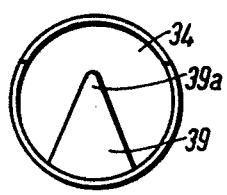
FIG. 3 shows an end view of the embodiment according to FIGS. 1 and 2.

In FIGS. 1 and 2 there is shown a needle 30 according to the invention made of thin-walled metal and made in one piece. The front end of the needle, which extends over about 1/6 of the length of the needle, is designed with a closed, conically tapered end portion 31 which passes directly over into a first cylindrical, central pipe portion 32 which extends over about ½ of the length of the needle. Over the last ⅓ of the length of the needle there is shown another pipe portion 33 with an elongate, laterally directed opening 34. As shown in FIG. 3, the opening 34 extends over about ⅓ of the periphery of the pipe, the edge portions 35, 36, which define the opening 34 in the peripheral direction of the pipe and which converge towards each other, being adapted to form clamping means or holding means for securing outer end 11a of the line 11 after it is fixed in position in the pipe portions 32, 33. In FIG. 1 there is illustrated in full lines outer end 11a of the line 11 after it is pushed into the opening 34 in the direction of the arrow 37 and further inwards in the portion 32 coaxially with the main axis of the needle. In broken lines the line is shown after it has been placed in position in locking engagement with a locking means fixed to the inner bottom side 38 of the pipe portion 33, that is to say the side which lies directly opposite the opening 34. The locking means is in the form of a hook portion 39, which extends obliquely upwards and obliquely outward from the bottom side 38 towards an end edge 40 which forms an inner boundary edge for the opening 34. The distance a between the outer end of the hook portion 39 and the edge 40 is greater than the cross-sectional dimension of the line 11, preferably not substantially larger than this cross-sectional dimension, but nevertheless so much larger that the line can be introduced inwardly into the pipe portion 32 without being substantially hindered by outer end 39a of the hook portion 39 on introduction of the line end 11a in the direction of the arrow 37 and while the line takes up a laterally somewhat squeezed together cross-sectional form as determined by the edge portions 35, 36. The outer end 40 of the hook portion 39 is arranged at a distance of about 1/6 of the length of the needle from the rear edge 41 of the needle.

In the illustrated embodiment according to FIGS. 1–3 the hook portion 39 is stamped from the bottom side 38 of the pipe portion 33 and extends obliquely upwards and outward at an angle of about 45° relative to the longitudinal direction of the needle. The outer end 39a is terminated at a level close by, that is to say in the illustrated embodiment just below a plane through the edge portions 35, 36. At the root portion the hook portion has a breadth of about ½ the diameter of the pipe portion, while the outer end of the hook portion is terminated with a tapered, but somewhat rounded-off end portion.

Figure 4:
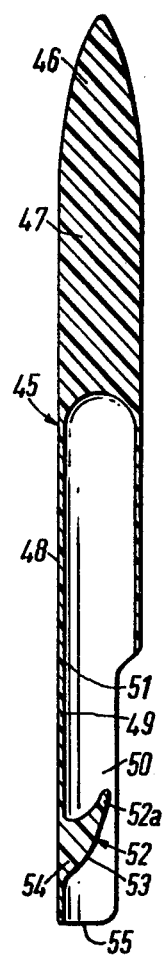
FIG. 4 shows another embodiment of the needle made of die cast plastic, shown in longitudinal section.
Figure 5:
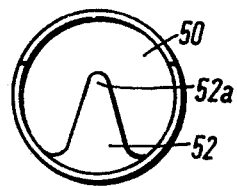
FIG. 5 shows an end view of the embodiment according to FIG. 4.

In the embodiment according to FIG. 4 and 5 there is shown a needle 45 made of die cast plastic and designed in one piece. The front end of the needle is fashioned in a manner corresponding to that of FIGS. 1 and 2 with a closed, conically tapered end portion 46. The needle has over about ⅓ of the length of the needle a compact, relatively rigid portion 47 which comprises said tapered end portion 46. From the compact portion 47 the needle extends further backwards with a cylindrical portion 48 over a length of somewhat less than ⅓ of the length of the needle, and from the pipe-shaped portion 48 the needle continues with a pipe-shaped portion 49 with a laterally directed, elongate opening 50. The opening 50 is cut out in a manner corresponding to the opening 34 of FIGS. 1–3 over a distance of about ⅓ of the periphery of the pipe. In the bottom side 51 directly opposite the opening 50 there is remetalled a hook portion 52 with a reinforced back portion 53 and below a reinforced root portion 54. The outer end 52a of the hook portion 52 is tapered in a manner corresponding to the outer end 39a of the hook portion 39, but has a somewhat rounded-off end portion. The rear edge of the pipe portion is shown at 55.

Figure 6:
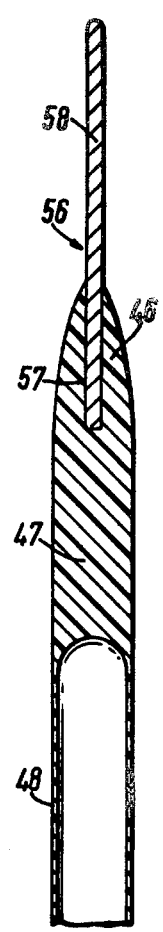
FIG. 6 shows a detail in the head portion of the needle according to FIGS. 4 and 5.

According to FIG. 6 there is shown an alternative construction of the front end of the needle according to FIGS. 4 and 5. In the foremost portion of the compact, relatively rigid portion 47 there is inserted a metal pin 56, the root portion 57 of which is moulded into the die cast plastic material. The root portion 57 of the metal pin is adapted to reinforce the front end of the needle specifically. Axially behind the root portion of the metal pin the needle can (if it is made of soft plastic) be somewhat elastically yielding, while the subsequent, pipeshaped portions of the needle are further elastically yielding, so that there is the possibility for controlled deflecting of the needle in its longitudinal direction, when this is desirable. In the rear portion 49 of the needle, where there is cut out the opening 50 and where the needle is especially elastically yielding, the pipe cross-section can if desired be somewhat deformed in order to obtain an extra gripping effect against the line.

By means of the outwardly projecting pin portion 58 of the needle there is the possibility of forcing the needle in a ready manner inwards into or through the line portion which is to be spliced or passing it through another line portion and starting a path for the subsequent larger size portion, it being preferred in certain cases to introduce the needle through the line in an arbitrary location or manner, for example between accidental hook portions in the line or accurately between braided portions or twists in the line.

When the finishing of the line is described above, it is to be understood also that cordage can also be similarly finished. In particular it is necessary to splice the strand portion in a braided cordage simply by means of the needle according to the invention. The splicing of braided cordage is effected in a manner substantially corresponding to that for the plaited line, the only difference being that the individual strand ends are spliced instead of the line end.

I claim:

1. A unitary needle device for finishing and splicing lines or cordage, consisting essentially of:

a unitary member of substantially cylindrical configuration;

said unitary member having a tapered front end portion, a tubular middle portion having a substantially continuous circumference and adapted to receive a strand end, and a substantially tubular rear portion;

said rear portion comprising an elongated lateral opening adapted for insertion of said strand and an integral hook internal of said rear portion opposite said lateral opening;

said hook extending from a base portion thereof located adjacent the rear end of said unitary member obliquely toward said lateral opening and toward said middle portion of said unitary member, said hook comprising a tip portion positioned generally opposite the rear-most part of said middle portion of said unitary member and spaced there-from a distance sufficient to permit insertion of said strand into said middle portion, whereby said strand is insertable axially thereof into said middle portion through said lateral opening and laterally engageable with said hook through said lateral opening for retention in said unitary member.

2. The unitary device of claim 1, wherein said lateral opening extends about substantially less than one-half of the periphery of said rear portion, said unitary member defining converging longitudinal edges of said lateral opening for securing said strand in engagement with said hook.

3. The unitary device of claim 2, consisting of material which is elastically yieldable in at least said rear portion whereby said longitudinal edges yield for insertion of said strand and are yieldably biased against a strand maintained in engagement with said hook.

4. The unitary device of claim 1, consisting of material which is elastically yieldable in at least said rear portion.

5. The unitary device of claim 1, wherein said tapered front end portion is solid.

6. The unitary device of claim 1, wherein said tapered front end portion is tubular.

7. The unitary device of claim 1, consisting of a unitary metal member, said hook being stamped from said unitary metal member.

8. The unitary device of claim 1, consisting of a unitary molded element.

* * * * *